US00PP10280P

United States Patent [19]

Brown

[11] Patent Number: Plant 10,280

[45] Date of Patent: Mar. 10, 1998

[54] AGLAONEMA PLANT NAMED 'BLACK LANCE'

[75] Inventor: B. Frank Brown, Valkaria, Fla.

[73] Assignee: Sunshine Foliage World, Zolfo Springs, Fla.

[21] Appl. No.: 751,866

[22] Filed: Nov. 18, 1996

[51] Int. Cl.[6] ..... P01H 8/00

[52] U.S. Cl. ..... Plt./88.1

[58] Field of Search ..... Plt./88.1

*Primary Examiner*—James R. Feyrer
*Assistant Examiner*—Elizabeth C. Kemmerer
*Attorney, Agent, or Firm*—C. A. Whealy

[57] ABSTRACT

A new and distinct cultivar of Aglaonema named 'Black Lance' particularly characterized by its tall, upright and freely branching plant habit; long and narrow tri-colored leaves centrally marked with two shades of silver green; rapid growth rate; and resistant to diseases common to Aglaonema.

2 Drawing Sheets

The present invention relates to a new and distinct cultivar of Aglaonema plant, botanically known as *Aglaonema hybrida*, and hereinafter referred to by the cultivar name Black Lance.

The new cultivar is a product of a planned breeding program conducted by the inventor in Valkaria, Fla. The new cultivar originated from a cross by the inventor between the species *Aglaonema simplex* as the female, or seed, parent with the nonpatented cultivar *Aglaonema hybrida* 'Ernesto's Favorite'. The cultivar Black Lance was discovered and selected by the inventor in August, 1988, as a plant within the progeny of the stated cross in a controlled environment in Valkaria, Fla.

Asexual propagation of the new cultivar by divison Valkaria, Fla., has shown that the unique features of this new Aglaonema plant are stable and reproduced true to type in successive generations of asexual propagation.

The new Aglaonema has not been observed under all possible environmental conditions. The phenotype may vary somewhat with variations in environment such as temperature, light intensity and fertilizer rate, without, however, any variance in genotype. The following observations, measurements and comparisons describe plants grown in Zolfo Springs, Fla., under a polypropylene-covered shadehouse and conditions which closely approximate those used in horticultural practice.

The following traits have been repeatedly observed and are determined to be the unique characteristics of 'Black Lance'. These characteristics in combination distinguish 'Black Lance' as a new and distinct cultivar:

1. Plants of the new Aglaonema are relatively tall, upright and freely branching.
2. The leaves of the new Aglaonema are relatively long and narrow.
3. The abaxial leaf surfaces of plants of the new Aglaonema are marked with three shades of green. The base color is very dark green and the center of the leaf is silver green with lighter silver green chevrons which follow the primary veins.
4. Plants of the new Aglaonema have a rapid growth rate.
5. Plants of the new Aglaonema are exceptionally resistant to diseases common to Aglaonema.

Plants of the new Aglaonema can be compared to plants of the Aglaonema cultivar Rhapsody in Green (disclosed in U.S. Plant Pat. No. 8,975) which have a similar leaf color pattern and growth habit. However, leaves of plants of the new Aglaonema are marked with three shades of green, and are much darker green in base color compared to leaves of plants of the cultivar Rhapsody in Green that have lighter green bi-colored leaves. In addition, plants of the new Aglaonema are more freely branching than plants of the cultivar Rhapsody in Green.

The accompanying colored photographs illustrate the overall appearance of the new cultivar, showing the colors as true as it is reasonably possible to obtain in colored reproductions of this type.

The first photograph comprises a top perspective view of a typical single plant of 'Black Lance' in a 26-cm container about 16 months after planting a single four-leaf cutting.

The second photograph comprises a close-up view of the abaxial (left) and adaxial (right) surfaces of a mature leaf and illustrates the detail of the leaf color pattern. Leaf colors in the photographs may appear different from the actual colors due to light reflectance.

In the following description, color references are made to The Royal Horticultural Society Colour Chart except where general terms of ordinary dictionary significance are used.

Botanical classification: *Aglaonema hybrida* cultivar Black Lance.

Parentage:

*Seed or female parent.*—*Aglaonema simplex.*

*Pollen or male parent.*—*Aglaonema hybrida* 'Ernesto's Favorite' (not patented).

Propagation: Asexual propagation by division or tissue culture.

Plant description:

*Plant shape.*—Tall, upright and outwardly spreading, symmetrical, dense and freely branching

*Growth habit.*—Erect when young, becoming more outwardly spreading as leaves develop.

*Plant size.*—Height: Soil surface to top of leaf canopy: Approximately 65 to 72 cm. Soil surface to junction of the petioles of the last two unrolled leaves: Approximately 26 to 32 cm. Width: Approximately 88 to 94 cm.

*Root description.*—Thick white roots with fine laterals.

*Stem description.*—Upright. Diameter, 5 cm above the soil surface: Approximately 1.5 to 1.7 cm. Internode length, 3 cm above the soil surface: Approximately 2.1 to 2.2 cm. Color: 147A lightly mottled with 147B/147C with areas of 164B/164C.

*Petiole description.*—following description is based on the fourth expanded leaf from the apex. Growth pattern: The petiole has fleshy edges extending from the midrib that are referred to as wings. Wings extend from the base of the petiole to approximately 10 to 12.4 cm below the base of the leaf. The wings are about 3 to 4 mm wide midway from the petiole base to the wing apex. The wing apex is acutely tapered and becomes flush with the petiole. The petiole follows the stem axis but diverges from the axis about 19.2 cm to 22.5 cm from the leaf base, forming a horizontal distance from the vertical axis of the stem to the leaf base of 7.2 cm to 12.4 cm. Dimensions: The petiole is straight from its base to the tip of the wings, and often curved between the tip of the wings and the base of the leaf. The petiole is approximately 4 mm to 5 mm in diameter midway between the wing apex and the base of the leaf. The petiole is approximately 19.8 cm to 24.8 cm in length from its base to the base of the leaf. Color: The petiole wings are 147A with small streaks of 147D. The petiole midrib is darker than 147B.

*Leaf description.*—Axillary breaks: There are approximately 16 axillay breaks with at least one leaf expanded. First leaves will show true color and color pattern. Growth Pattern: The leaf is long and narrow in shape with an acute to acuminate apex and an acute base. The margin is entire. The leaf is oriented parallel to the stem axis at the time of full unrolling, changing to approximately 40 to 60 degrees from vertical stem axis as more leaves unroll above it. The midrib is straight. The leaf blade is fiat from the midrib to the margin and often wavy along the margin. Dimensions: For the pot size and growing time indicated, the largest leaves are approximately 29.5 cm to 32.6 cm long and approximately 8.4 cm to 9.2 cm wide. Average sized leaves are approximately 24.8 cm to 26.6 cm long and approximately 5.0 cm to 5.5 cm wide. The leaf blade is leathery in texture with a matte to slightly glossy surface. Midrib: The midrib is thick and prominent, recessed on the abaxial leaf surface and prominent on the adaxial surface. Primary veins: The primary veins are sunken on the abaxial surface and are slightly prominent on the adaxial surface. The primary veins are the same color as the tissue surrounding them. The leaf blade is convex between the primary veins. Pattern: The abaxial leaf surface is marked with three shades of green. The base color of the leaf is very dark green, the center of the leaf is silver green with lighter silver green chevrons which follow the primary veins. The lighter silver green chevrons are most obvious on newly emerged leaves, and fade as the leaf matures. The adaxial leaf surface is medium green with pale silver green markings along the primary veins. Color: Mature leaf, abaxial surface: Base color: Much darker than 147A. Silver green central areas: 191A. Lighter silver green chevrons: 191B/191C. Midrib: 191A. Mature leaf, adaxial surface: Base color: Darker than 147B. Pale silver green markings: 147C. Midrib: 146D. Newly opened leaf, abaxial surface: Base color: 147A. Silver green central areas: 191A. Lighter silver green markings: 193A. Midrib: 191A. Newly opened leaf, adaxial surface: Base color: 147B with pale silver green markings of 147C. Midrib: 146D.

*Inflorescence.*—Typical of Aglaonema, no commercial significance.

GENERAL OBSERVATIONS

Aglaonema Black Lance is a freely branching, relatively upright and tall growing variety having long narrow tricolored leaves with a prominent silver green center and lighter silver green chevrons. Plants of Black Lance have a rapid growth rate, and are exceptionally resistant to diseases common to Aglaonema. These characteristics in combination make Black Lance a distinct and unique new cultivar.

It is claimed:

1. A new and distinct cultivar of Aglaonema plant named 'Black Lance', as illustrated and described.

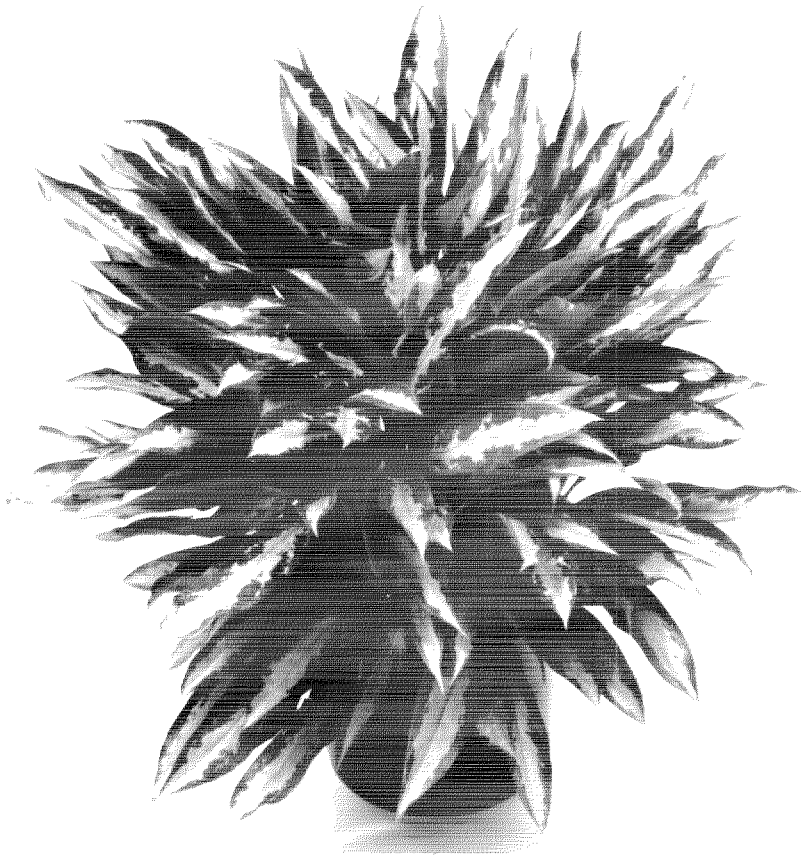

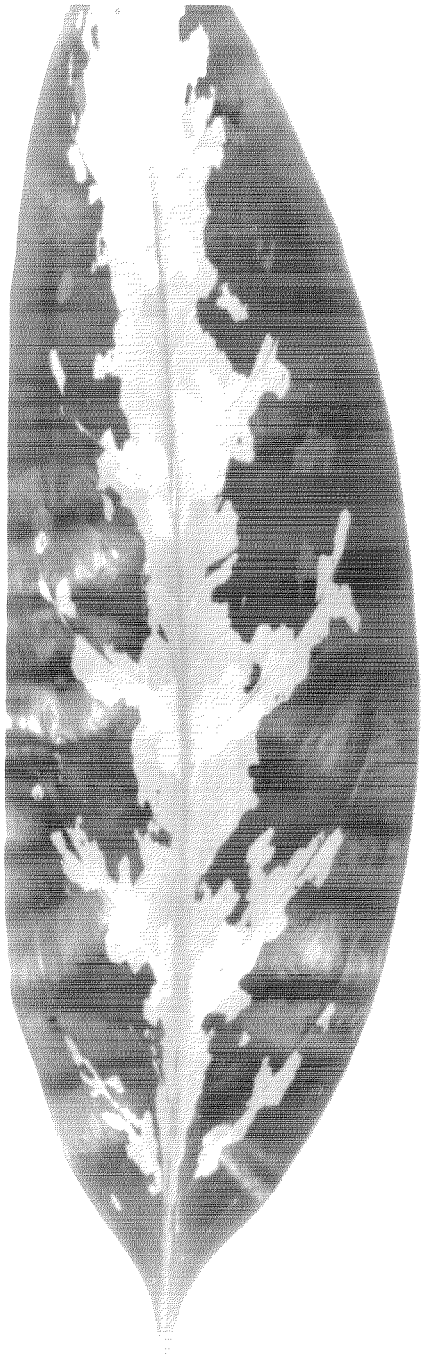
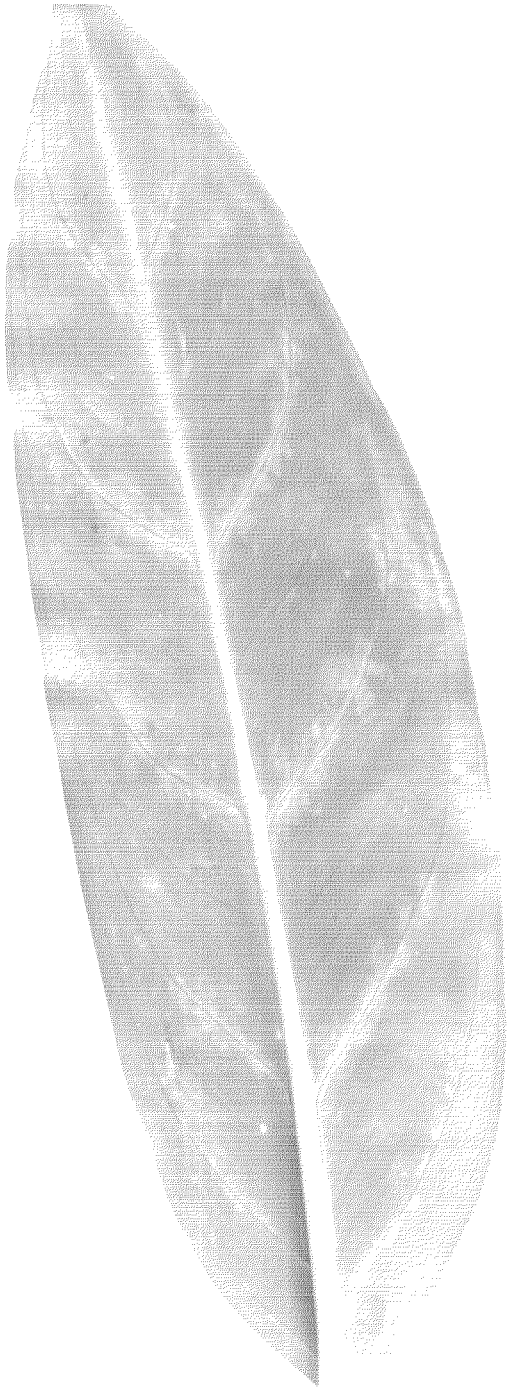

* * * * *